United States Patent
Bhattacharyya et al.

(10) Patent No.: US 9,223,227 B2
(45) Date of Patent: Dec. 29, 2015

(54) INSPECTION APPARATUS AND METHOD, LITHOGRAPHIC APPARATUS, LITHOGRAPHIC PROCESSING CELL AND DEVICE MANUFACTURING METHOD

(75) Inventors: Kaustuve Bhattacharyya, Veldhoven (NL); Arie Jeffrey Den Boef, Waalre (NL); Stefan Carolus Jacobus Antonius Keij, Breda (NL); Peter Clement Paul Vanoppen, Hechtel-Eksel (BE)

(73) Assignee: ASML Netherlands B.V., Veldhoven (NL)

( * ) Notice: Subject to any disclaimer, the term of this patent is extended or adjusted under 35 U.S.C. 154(b) by 1005 days.

(21) Appl. No.: 13/361,349

(22) Filed: Jan. 30, 2012

(65) Prior Publication Data

US 2012/0206703 A1     Aug. 16, 2012

Related U.S. Application Data

(60) Provisional application No. 61/442,145, filed on Feb. 11, 2011.

(51) Int. Cl.
| | |
|---|---|
| *G03B 27/54* | (2006.01) |
| *G03F 7/20* | (2006.01) |
| *G01N 21/956* | (2006.01) |

(52) U.S. Cl.
CPC ........... *G03F 7/70625* (2013.01); *G03F 7/705* (2013.01); *G03F 7/70633* (2013.01); *G01B 2210/56* (2013.01); *G01N 21/956* (2013.01)

(58) Field of Classification Search
CPC . G03F 7/705; G03F 7/70625; G03F 7/70633; G01N 21/956; G01B 2210/56
See application file for complete search history.

(56) References Cited

U.S. PATENT DOCUMENTS

| | | | |
|---|---|---|---|
| 4,170,401 A | 10/1979 | Yoder, Jr. et al. | |
| 4,541,720 A | 9/1985 | Häusler et al. | |

(Continued)

FOREIGN PATENT DOCUMENTS

| | | |
|---|---|---|
| CN | 101251718 B | 9/2010 |
| CN | 101819384 A | 9/2010 |

(Continued)

OTHER PUBLICATIONS

Dürr et al., "An advanced study for defect disposition through 193nm aerial imaging," *SPIE Proceedings*, vol. 6152, published Mar. 24, 2006; 9 pages.

(Continued)

*Primary Examiner* — Deoram Persaud
(74) *Attorney, Agent, or Firm* — Sterne, Kessler, Goldstein & Fox P.L.L.C.

(57) ABSTRACT

Asymmetry properties of a periodic target on a substrate, such as a grating on a wafer, are determined. An inspection apparatus has a broadband illumination source with illumination beams point mirrored in the pupil plane of a high numerical aperture objective lens. The substrate and target are illuminated via the objective lens from a first direction and a second direction mirror reflected with respect to the plane of the substrate. A quad wedge optical device separately redirects diffraction orders of radiation scattered from the substrate and separates diffraction orders from illumination along each of the first and second directions. For example the zeroth and first orders are separated for each incident direction. After capture in multimode fibers, spectrometers are used to measure the intensity of the separately redirected diffraction orders as a function of wavelength.

21 Claims, 13 Drawing Sheets

(56) References Cited

U.S. PATENT DOCUMENTS

| | | | | |
|---|---|---|---|---|
| 5,703,692 | A * | 12/1997 | McNeil | G01N 21/474 356/445 |
| 6,628,406 | B1 | 9/2003 | Kreuzer | |
| 6,819,434 | B2 * | 11/2004 | Hill | G01B 11/26 356/493 |
| 6,961,116 | B2 | 11/2005 | Den Boef et al. | |
| 7,362,446 | B2 * | 4/2008 | Van Der Pasch | G03F 7/70775 355/53 |
| 7,468,795 | B2 | 12/2008 | Simons et al. | |
| 7,511,826 | B2 * | 3/2009 | Kreuzer | G03F 9/7069 356/509 |
| 7,701,577 | B2 | 4/2010 | Straaijer et al. | |
| 8,339,595 | B2 | 12/2012 | Den Boef | |
| 2003/0021467 | A1 * | 1/2003 | Adel | G03F 7/70633 382/151 |
| 2004/0033426 | A1 * | 2/2004 | Den Boef et al. | 430/22 |
| 2004/0130690 | A1 * | 7/2004 | Koren | G03F 7/7046 355/53 |
| 2005/0195398 | A1 * | 9/2005 | Adel | B82Y 10/00 356/401 |
| 2006/0126074 | A1 * | 6/2006 | Van Der Werf | G01N 21/211 356/489 |
| 2007/0296973 | A1 * | 12/2007 | Kiers | G01N 21/21 356/369 |
| 2008/0013090 | A1 | 1/2008 | Hagiwara | |
| 2008/0198380 | A1 * | 8/2008 | Straaijer et al. | 356/369 |
| 2008/0239318 | A1 | 10/2008 | Den Boef et al. | |
| 2009/0040490 | A1 | 2/2009 | Shigematsu et al. | |
| 2010/0201963 | A1 | 8/2010 | Cramer et al. | |
| 2010/0328655 | A1 | 12/2010 | Den Boef | |
| 2011/0164228 | A1 | 7/2011 | Van De Kerkhof | |
| 2012/0033226 | A1 | 2/2012 | Manassen et al. | |
| 2013/0271740 | A1 * | 10/2013 | Quintanilha | G03F 1/144 355/67 |

FOREIGN PATENT DOCUMENTS

| | | |
|---|---|---|
| CN | 101903832 A | 12/2010 |
| EP | 1 628 164 A2 | 2/2006 |
| JP | 06-147827 A | 5/1994 |
| JP | 2000-275569 A | 10/2000 |
| JP | 2007-114655 A | 5/2007 |
| TW | 200710596 A | 3/2007 |
| TW | 200951641 A | 12/2009 |
| WO | WO 2009/000456 A1 | 12/2008 |

OTHER PUBLICATIONS

English-Language Abstract for Japanese Patent Publication No. 2000-275569, published Oct. 6, 2000; 1 page.

English-Language Abstract for Japanese Patent Publication No. 2007-114655, published May 10, 2007; 1 page.

English-Language Abstract for International Patent Publication No. 2009/000456 A1, published Dec. 31, 2008; 1 page.

English-Language Abstract for Japanese Patent Publication No. 06-147827 A, published May 27, 1994; 1 page.

* cited by examiner

INSPECTION APPARATUS AND METHOD, LITHOGRAPHIC APPARATUS, LITHOGRAPHIC PROCESSING CELL AND DEVICE MANUFACTURING METHOD

CROSS REFERENCE TO RELATED APPLICATIONS

This application claims the benefit under 35 U.S.C. §119 (e) to U.S. Provisional Patent Application No. 61/442,145, filed Feb. 11, 2011, which is incorporated by reference herein in its entirety.

FIELD

The present invention relates to apparatus and methods for determining asymmetry in microstructures usable, for example, in the manufacture of devices by lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Image-based overlay metrology is currently a mainstream overlay metrology technique. Diffraction Based Overlay (DBO) is, however, gaining momentum and acceptance at semiconductor manufacturers as the need for better precision increases.

A large contributor to the accuracy of on-product overlay metrology is asymmetric grating deformation. Asymmetry in the profile of etched structures can, for example, result if etchant ions are not incident perpendicular to the substrate while etching. It is desirable to provide an inspection apparatus to allow overlay measurements, asymmetry measurements and reconstruction on small in-die overlay targets that are needed by manufacturers for on-product overlay metrology.

Furthermore, it is desirable to improve the TMU and acquisition time of such an inspection apparatus.

SUMMARY

According to an aspect of the present invention, there is provided an inspection apparatus for determining asymmetry properties of a target on a substrate, the target being periodic in a plane of the substrate. The inspection apparatus comprises an illumination system configured to provide a plurality of wavelengths of radiation, an optical system comprising an objective and configured to illuminate the target via the objective with the radiation from a first direction and a second direction mirror reflected with respect to the plane of the substrate, an optical device configured to separately redirect diffraction orders of radiation scattered from the substrate, one or more detectors configured to measure properties of the separately redirected diffraction orders at the plurality of wavelengths, and a processor configured determine asymmetry properties of the target using the properties measured at the plurality of wavelengths.

According to another aspect of the present invention, there is provided a method of determining asymmetry properties of a target on a substrate, the target being periodic in a plane of the substrate. The method comprises providing a plurality of wavelengths of radiation, illuminating the target via an objective with the radiation from a first direction and a second direction mirror reflected with respect to the plane of the substrate, separately redirecting diffraction orders of radiation scattered from the substrate, measure properties of the separately redirected diffraction orders at the plurality of wavelengths using one or more detectors, and determining asymmetry properties of the target using the properties measured at the plurality of wavelengths.

According to another aspect of the present invention, there is provided a lithographic apparatus comprising an illumination system arranged to illuminate a pattern, a projection system arranged to project an image of the pattern on to a substrate, and an inspection apparatus for determining asymmetry properties of a target on a substrate, the target being periodic in a plane of the substrate. The inspection apparatus comprises an illumination system configured to provide a plurality of wavelengths of radiation, an optical system comprising an objective and configured to illuminate the target via the objective with the radiation from a first direction and a second direction mirror reflected with respect to the plane of the substrate, an optical device configured to separately redirect diffraction orders of radiation scattered from the substrate, one or more detectors configured to measure properties of the separately redirected diffraction orders at the plurality of wavelengths, and a processor configured determine asymmetry properties of the target using the properties measured at the plurality of wavelengths.

According to another aspect of the present invention, there is provided a lithographic cell comprising: a coater arranged to coat substrates with a radiation sensitive layer, a lithographic apparatus arranged to expose images onto the radiation sensitive layer of substrates coated by the coater, a developer arranged to develop images exposed by the lithographic apparatus, and an inspection apparatus for determining asymmetry properties of a target on a substrate, the target being periodic in a plane of the substrate. The inspection apparatus comprises an illumination system configured to provide a plurality of wavelengths of radiation, an optical system comprising an objective and configured to illuminate the target via the objective with the radiation from a first direction and a second direction mirror reflected with respect to the plane of the substrate, an optical device configured to separately redirect diffraction orders of radiation scattered from the substrate, one or more detectors configured to measure properties of the separately redirected diffraction orders at the plurality of wavelengths, and a processor configured determine asymmetry properties of the target using the properties measured at the plurality of wavelengths.

According to another aspect of the present invention, there is provided a device manufacturing method comprising using a lithographic apparatus to form a pattern on a substrate, and determining a value related to a parameter of the pattern by providing a plurality of wavelengths of radiation, illuminating a target, formed using the lithographic apparatus, via an objective with the radiation from a first direction and a second direction mirror reflected with respect to the plane of the substrate, separately redirecting diffraction orders of radiation scattered from the substrate, measuring properties of the separately redirected diffraction orders at the plurality of wavelengths using one or more detectors, and determining asymmetry properties of the target using the properties measured at the plurality of wavelengths.

Further features and advantages of the present invention, as well as the structure and operation of various embodiments of the present invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the present invention and to enable a person skilled in the relevant art(s) to make and use the present invention.

Figure 1:
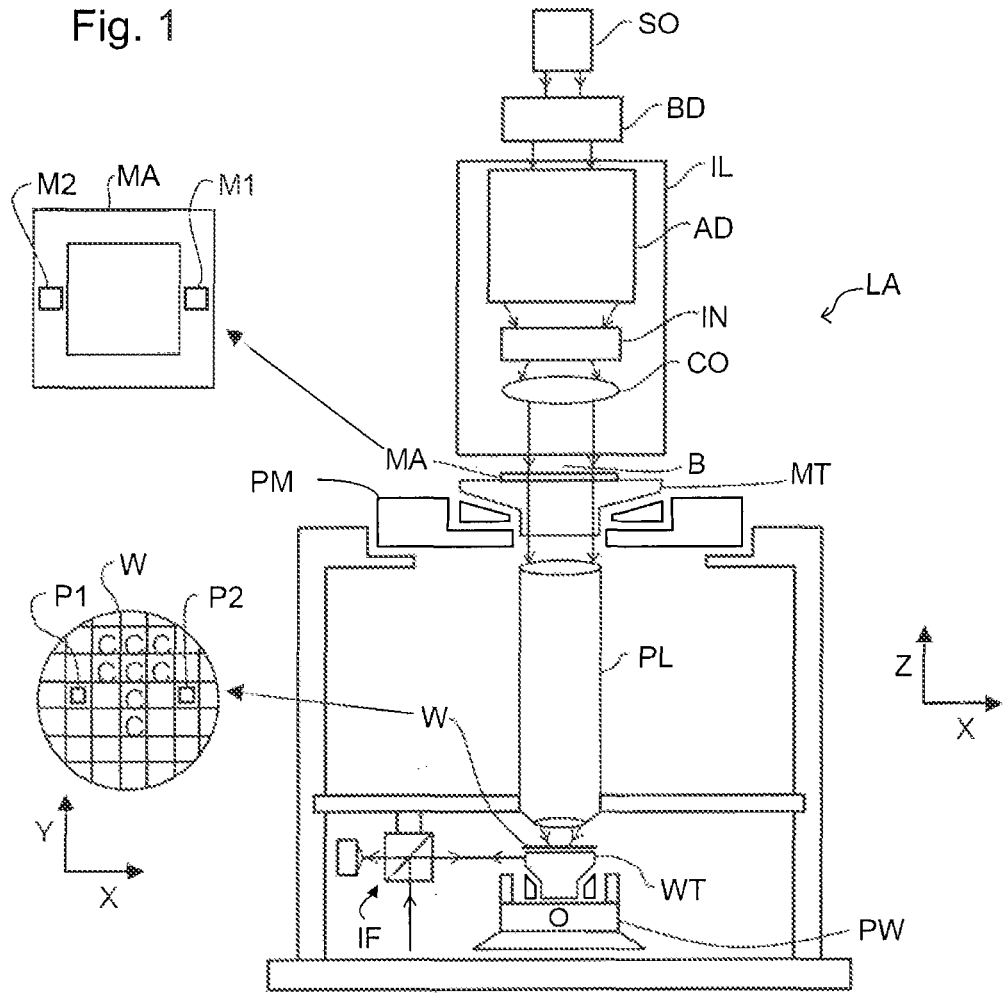
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically shows a lithographic apparatus LAP including a source collector module SO according to an embodiment of the present invention. The apparatus comprises an illumination system (illuminator) IL configured to condition a radiation beam B (e.g., EUV radiation); a support structure (e.g., a mask table) MT constructed to support a patterning device (e.g., a mask or a reticle) MA and connected to a first positioner PM configured to accurately position the patterning device; a substrate table (e.g., a wafer table) WT constructed to hold a substrate (e.g., a resist-coated wafer) W and connected to a second positioner PW configured to accurately position the substrate; and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
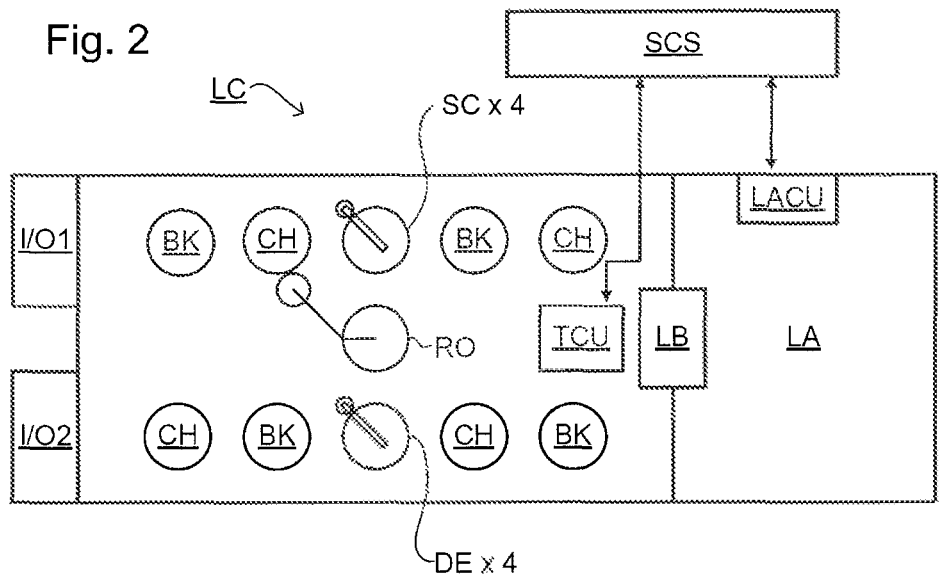
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
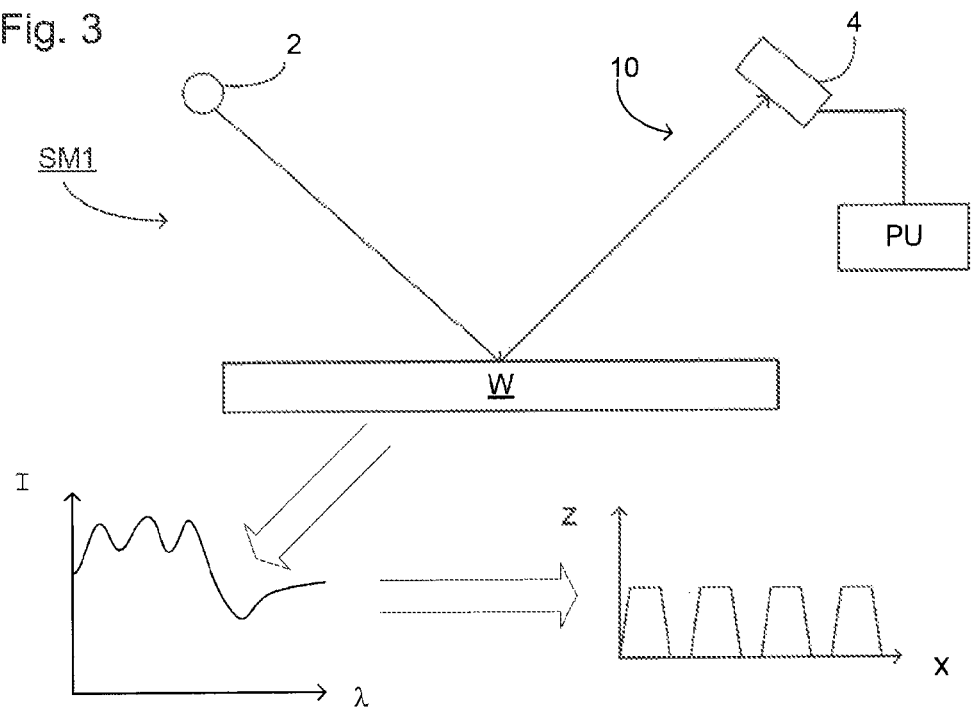
FIG. 3 depicts a first scatterometer.

FIG. 3 depicts a scatterometer which may be used in the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
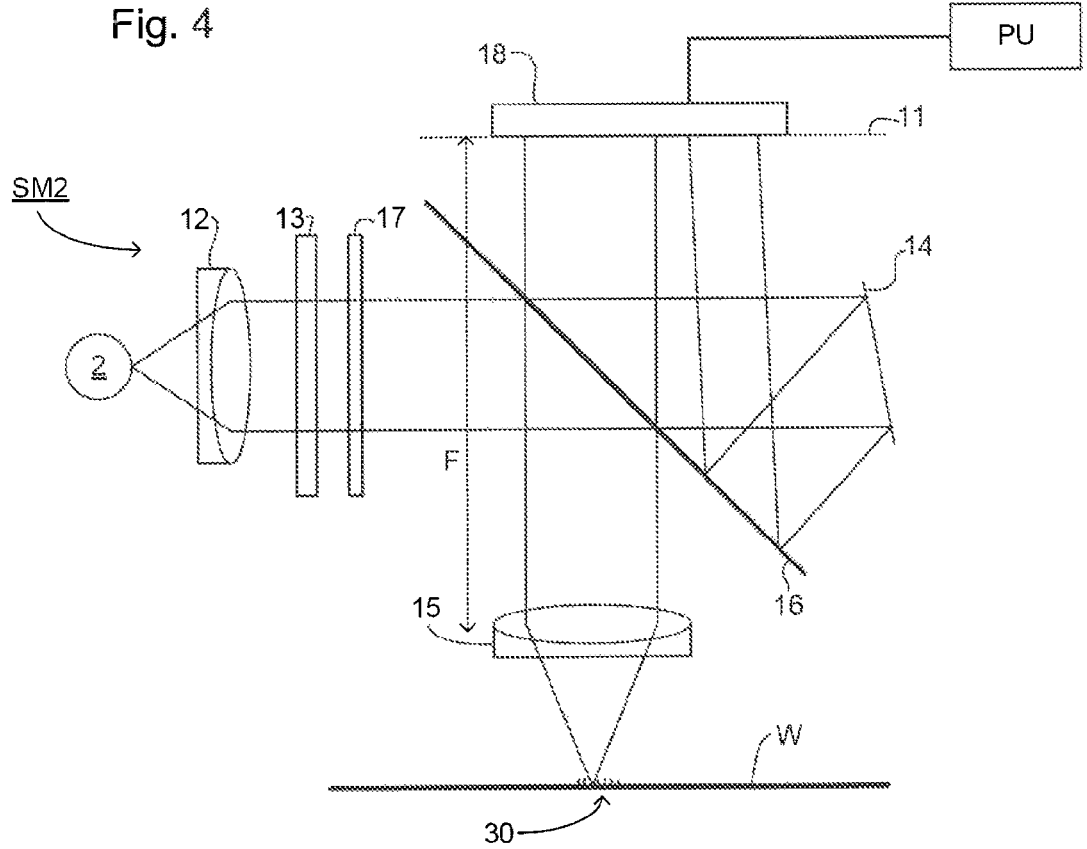
FIG. 4 depicts a second scatterometer.

Another scatterometer that may be used with the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein in its entirety.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Using one of the scatterometers described above in combination with modeling of a target structure such as the target 30 and its diffraction properties, measurement of the shape and other parameters of the structure can be performed in a number of ways. In a first type of process, represented by FIG. 5, a diffraction pattern based on a first estimate of the target shape (a first candidate structure) is calculated and compared with the observed diffraction pattern. Parameters of the model are then varied systematically and the diffraction re-calculated in a series of iterations, to generate new candidate structures and so arrive at a best fit. In a second type of process, represented by FIG. 6, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit.

In some applications, DBO is used for large gratings which provide the best total measurement uncertainty (TMU). On product wafers, manufacturers are pushing for smaller in-die targets. These gratings are measured with Dark Field (DF) detection at the expense of a slightly larger TMU. Diffraction Based Overlay and Dark Field detection are described in patent publication U.S. Pub. Appl. No 2010/0328655, which is incorporated by reference herein in its entirety.

Figure 5:
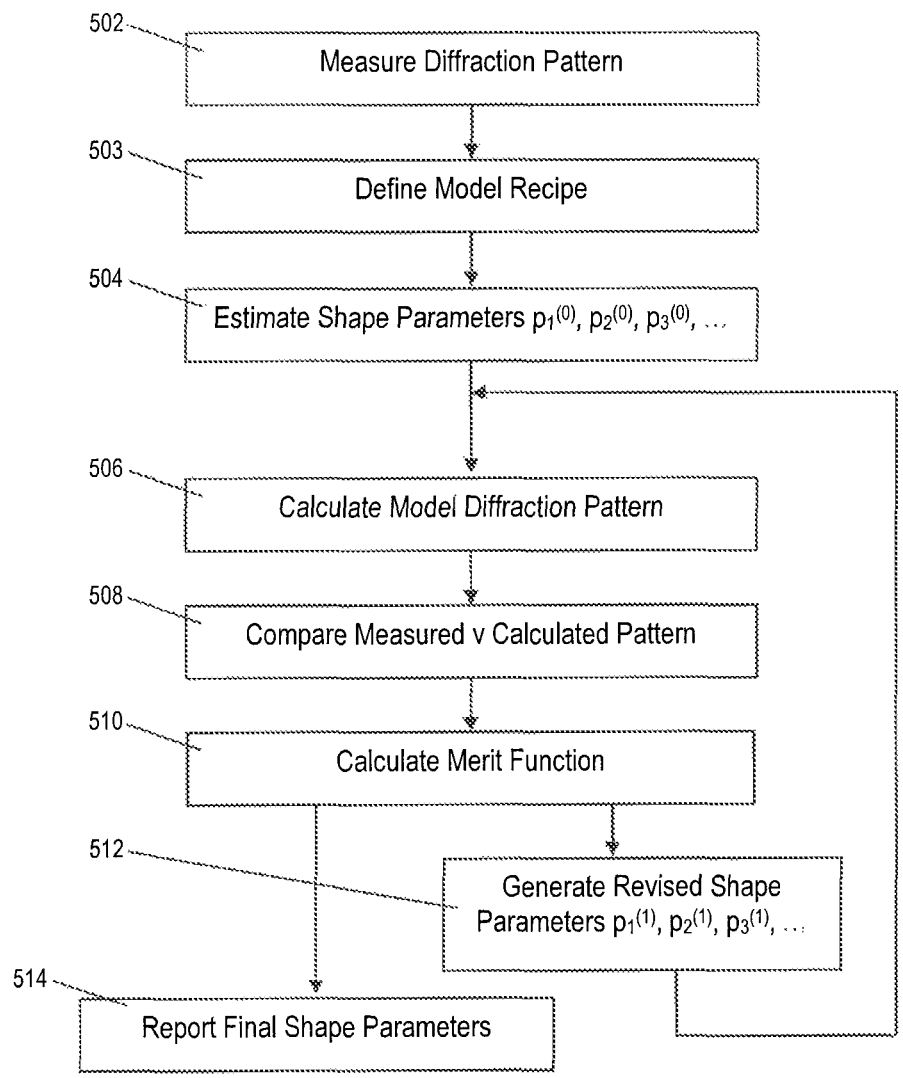
FIG. 5 depicts a first example process for reconstruction of a structure from scatterometer measurements.

Referring to FIG. 5 in more detail, the way the measurement of the target shape and/or material properties is carried out will be described in summary. The target will be assumed for this description to be periodic in only 1 direction (1-D structure). In practice it may be periodic in 2 directions (2-dimensional structure), and the processing will be adapted accordingly.

In step 502: The diffraction pattern of the actual target on the substrate is measured using a scatterometer such as those described above. This measured diffraction pattern is forwarded to a calculation system such as a computer. The calculation system may be the processing unit PU referred to above, or it may be a separate apparatus.

In step 503: A 'model recipe' is established which defines a parameterized model of the target structure in terms of a number of parameters $p_i$ ($p_1$, $p_2$, $p_3$ and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Specific examples will be given below. Importantly, while a target structure may be defined by dozens of parameters describing its shape and material properties, the model recipe will define many of these to have fixed values, while others are to be variable or 'floating' parameters for the purpose of the following process steps. Further below we describe the process by which the choice between fixed and floating parameters is made. Moreover, we shall introduce ways in which parameters can be permitted to vary without being fully independent floating parameters. For the purposes of describing FIG. 5, only the variable parameters are considered as parameters $p_i$.

In step 504: A model target shape is estimated by setting initial values $p_i^{(0)}$ for the floating parameters (i.e., $p_1^{(0)}$, $p_2^{(0)}$, $p_3^{(0)}$ and so on). Each floating parameter will be generated within certain predetermined ranges, as defined in the recipe.

In step 506: The parameters representing the estimated shape, together with the optical properties of the different elements of the model, are used to calculate the scattering properties, for example using a rigorous optical diffraction method such as RCWA or any other solver of Maxwell equations. This gives an estimated or model diffraction pattern of the estimated target shape.

In steps 508, 510: The measured diffraction pattern and the model diffraction pattern are then compared and their similarities and differences are used to calculate a "merit function" for the model target shape.

In step 512: Assuming that the merit function indicates that the model needs to be improved before it represents accurately the actual target shape, new parameters $p_1^{(1)}$, $p_2^{(1)}$, $p_3^{(1)}$, etc. are estimated and fed back iteratively into step 506. Steps 506-512 are repeated.

In order to assist the search, the calculations in step 506 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

514: When the merit function indicates that this iterative process has converged on a solution with a desired accuracy, the currently estimated parameters are reported as the measurement of the actual target structure.

The computation time of this iterative process is largely determined by the forward diffraction model used, i.e., the calculation of the estimated model diffraction pattern using a rigorous optical diffraction theory from the estimated target structure. If more parameters are required, then there are more degrees of freedom. The calculation time increases in principle with the power of the number of degrees of freedom. The estimated or model diffraction pattern calculated at 506 can be expressed in various forms. Comparisons are simplified if the calculated pattern is expressed in the same form as the measured pattern generated in step 502 For example, a modeled spectrum can be compared easily with a spectrum measured by the apparatus of FIG. 3; a modeled pupil pattern can be compared easily with a pupil pattern measured by the apparatus of FIG. 4.

Throughout this description from FIG. 5 onward, the term 'diffraction pattern' will be used, on the assumption that the scatterometer of FIG. 4 is used. The skilled person can readily adapt the teaching to different types of scatterometer, or even other types of measurement instrument.

Figure 6:
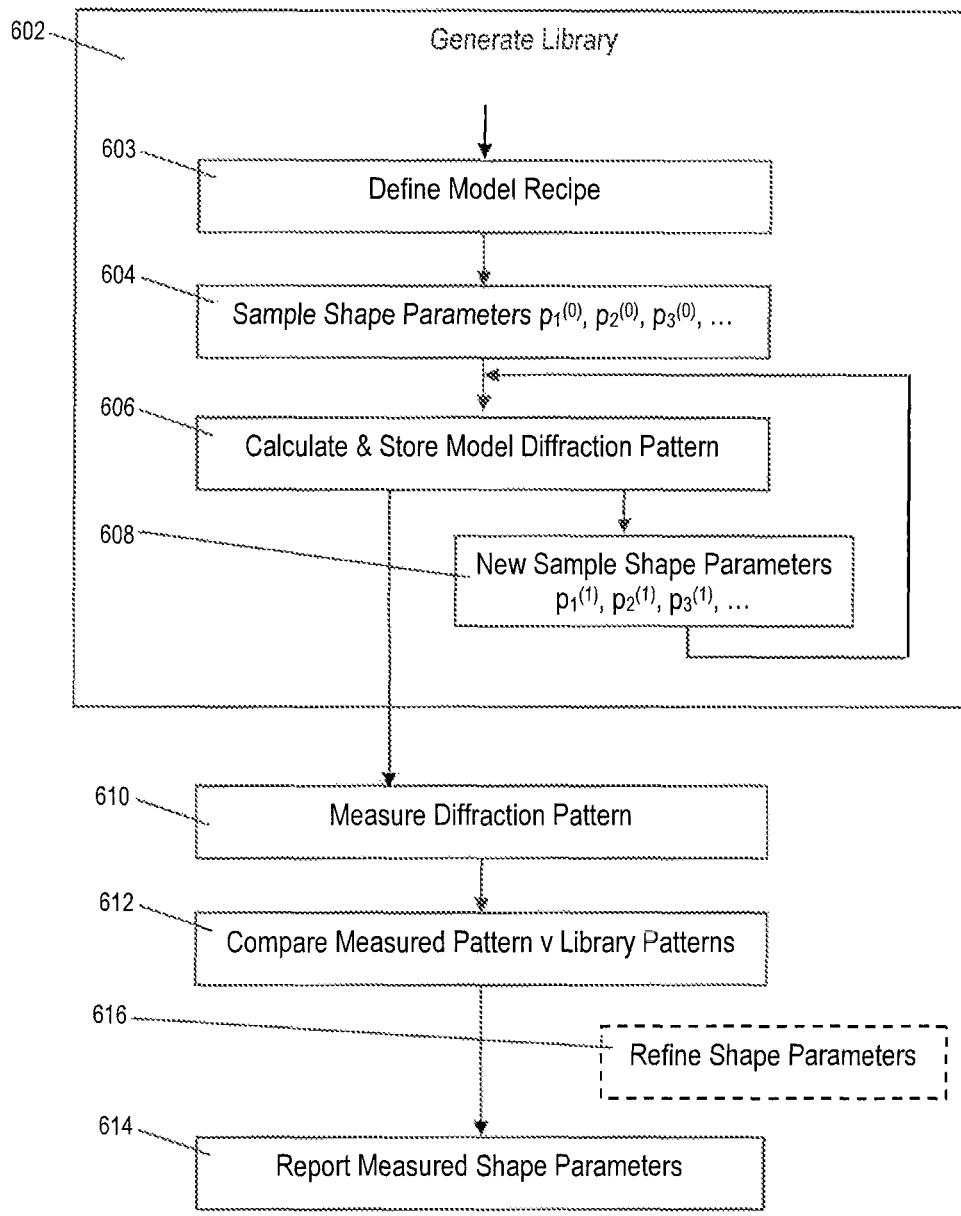
FIG. 6 depicts a second example process for reconstruction of a structure from scatterometer measurements.

FIG. 6 illustrates an alternative example process in which plurality of model diffraction patterns for different estimated target shapes (candidate structures) are calculated in advance and stored in a library for comparison with a real measurement. The underlying principles and terminology are the same as for the process of FIG. 5. The steps of the FIG. 6 process are:

In step 602: The process of generating the library begins. A separate library may be generated for each type of target structure. The library may be generated by a user of the measurement apparatus according to need, or may be pre-generated by a supplier of the apparatus.

In step 603: A 'model recipe' is established which defines a parameterized model of the target structure in terms of a number of parameters $p_i$ ($p_1$, $p_2$, $p_3$ and so on). Considerations are similar to those in step 503 of the iterative process.

In step 604: A first set of parameters $p_1^{(0)}$, $p_2^{(0)}$, $p_3^{(0)}$, etc. is generated, for example by generating random values of all the parameters, each within its expected range of values.

In step 606: A model diffraction pattern is calculated and stored in a library, representing the diffraction pattern expected from a target shape represented by the parameters.

In step 608: A new set of shape parameters $p_1^{(1)}$, $p_2^{(1)}$, $p_3^{(1)}$, etc. is generated. Steps 606-608 are repeated tens, hundreds or even thousands of times, until the library which comprises all the stored modeled diffraction patterns is judged sufficiently complete. Each stored pattern represents a sample point in the multi-dimensional parameter space. The samples in the library should populate the sample space with a sufficient density that any real diffraction pattern will be sufficiently closely represented.

In step 610: After the library is generated (though it could be before), the real target 30 is placed in the scatterometer and its diffraction pattern is measured.

In step 612: The measured pattern is compared with the modeled patterns stored in the library to find the best matching pattern. The comparison may be made with every sample in the library, or a more systematic searching strategy may be employed, to reduce computational burden.

In step 614: If a match is found then the estimated target shape used to generate the matching library pattern can be determined to be the approximate object structure. The shape parameters corresponding to the matching sample are output as the measured shape parameters. The matching process may be performed directly on the model diffraction signals, or it may be performed on substitute models which are optimized for fast evaluation.

In step 616: Optionally, the nearest matching sample is used as a starting point, and a refinement process is used to obtain the final parameters for reporting. This refinement process may comprise an iterative process very similar to that shown in FIG. 5, for example.

Whether refining step 616 is needed or not is a matter of choice for the implementer. If the library is very densely sampled, then iterative refinement may not be needed because a good match will always be found. On the other hand, such a library might be too large for practical use. A practical solution is thus to use a library search for a coarse set of parameters, followed by one or more iterations using the merit function to determine a more accurate set of parameters to report the parameters of the target substrate with a desired accuracy. Where additional iterations are performed, it would be an option to add the calculated diffraction patterns and associated refined parameter sets as new entries in the library. In this way, a library can be used initially which is based on a relatively small amount of computational effort, but which builds into a larger library using the computational effort of the refining step 616. Whichever scheme is used, a further refinement of the value of one or more of the reported variable parameters can also be obtained based upon the goodness of the matches of multiple candidate structures. For example, the parameter values finally reported may be produced by interpolating between parameter values of two or more candidate structures, assuming both or all of those candidate structures have a high matching score.

The computation time of this iterative process is largely determined by the forward diffraction model at steps 506 and 606, i.e., the calculation of the estimated model diffraction pattern using a rigorous optical diffraction theory from the estimated target shape.

The present invention relates to embodiments of apparatus for determining asymmetry properties of periodic targets, such as gratings.

Figure 7:
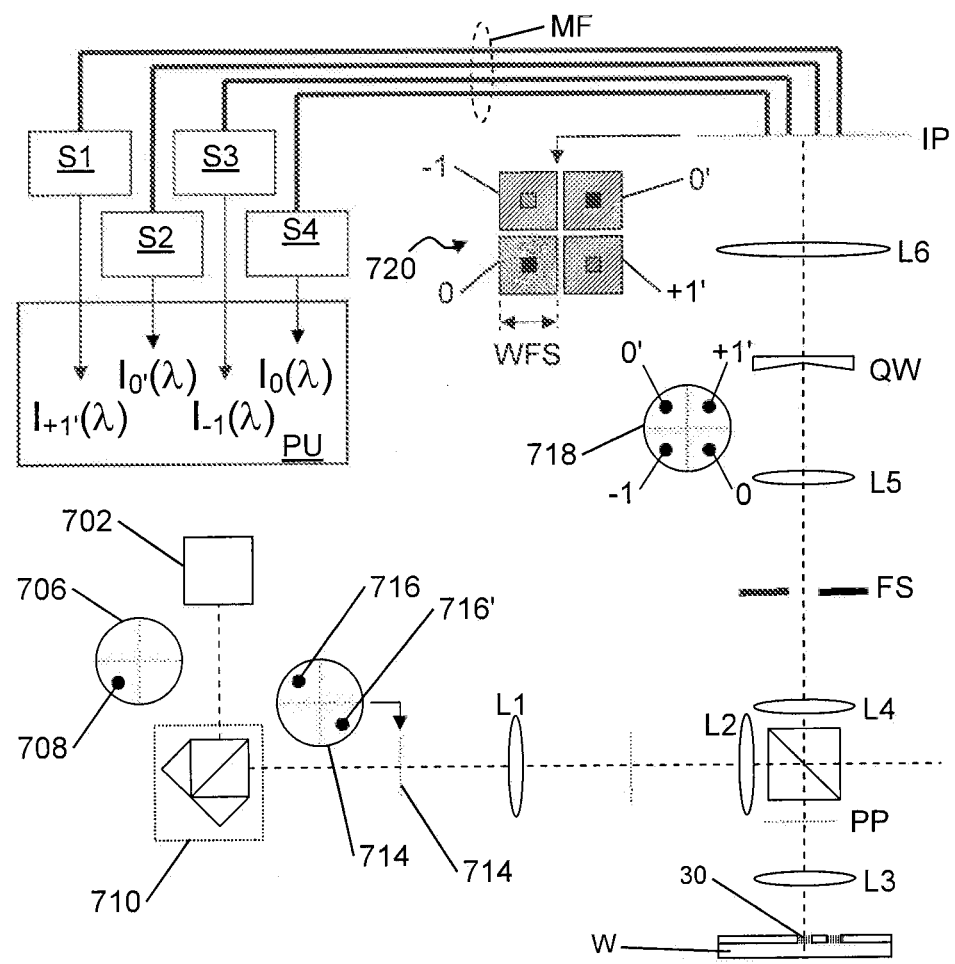
FIG. 7 illustrates an inspection apparatus according to an embodiment of the present invention.

FIG. 7 illustrates an inspection apparatus according to an embodiment of the present invention. With reference to FIG. 7, a broadband light source 702 provides a narrow pencil beam of white light, providing a plurality of wavelengths of radiation. The plurality of wavelengths are thus provided simultaneously, for fast measurement by the apparatus. In another embodiment, a tunable light source provides different wavelengths at different times. The light source 702 may, for example, be a white-light laser or a Xenon lamp. The illumination pupil 706 at the exit of the illuminator has one spot 708. The pencil beam is sent through an "image copy-and-rotate" device 710. This device makes a copy of the pencil beam and rotates the copied version over 180° relative to the original beam. An example of an "image copy-and-rotate" device is the self-referencing interferometer as described in U.S. Pat. Nos. 6,961,116 and 6,628,406, which are both incorporate by reference herein in their entireties.

As a result of this copy action, the illumination pupil plane 714 is now illuminated with two identical white-light sources 716, 716' that are point-mirrored relative to the origin (and have substantially zero spatial frequency). This provides a well-defined angle of incidence of illumination across the target that facilitates grating reconstruction. For this reason, the extent of the point sources is kept small.

Lenses L1 and L2 form a double-telecentric system that image the illumination pupil into the pupil plane of the high-NA (numerical aperture) lens L3. This objective lens L3 illuminates the target 30 which may be a small grating that is surrounded by an unknown product pattern. Lenses L1, L2 and L3 thus form an optical system that illuminates the target via the objective. The illumination spot on the wafer is normally chosen much larger than the grating. Typical values are, for example, a spot diameter of 30 µm projected on the wafer and grating size of 10×10 µm². The embodiment will still work when the illumination spot is smaller than the grating, for example with a relatively large grating in a scribe lane.

Figure 8:
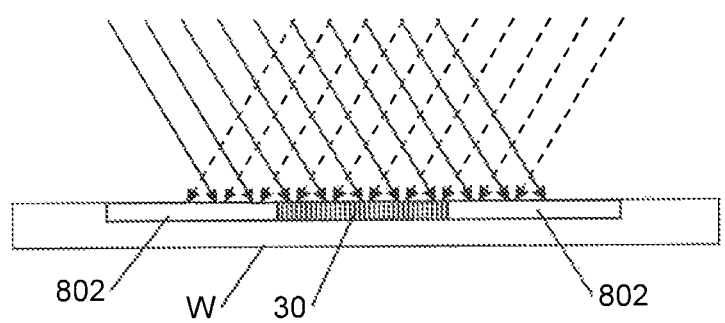
FIG. 8 illustrates light rays incident on the substrate.

FIG. 8 illustrates light rays incident on the substrate from a first direction and a second mirror reflected direction. The solid arrows represent light rays coming from point 716 in the illumination plane 714. The dashed arrows represent light rays coming from point 716' in the illumination plane 714. The substrate W has a target grating 30 surrounded by product areas 802. The illumination beam thus overfills the target grating 30. The solid arrows illuminate the grating under an angle of incidence such that they propagate along a direction substantially along a horizontal direction along the surface of the substrate, the substrate being in a fixed position. The dashed arrows illuminate the grating under the same angle of incidence such that they propagate along a direction substantially along the opposite horizontal direction along the surface of the substrate.

Figure 9:
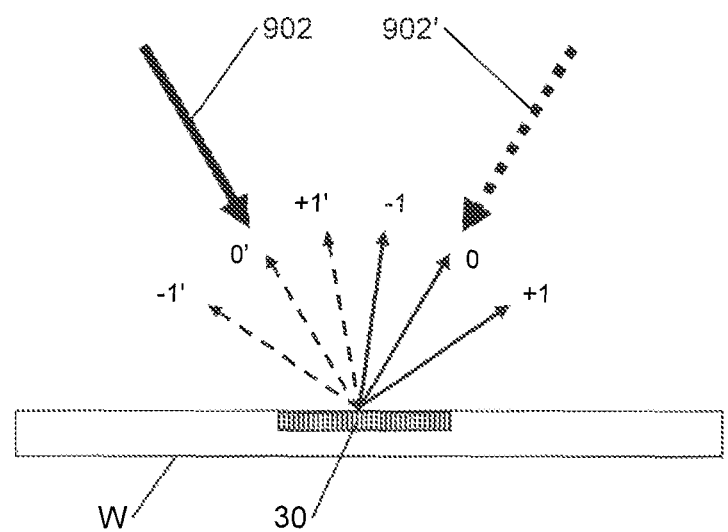
FIG. 9 illustrates two light beams incident on the target grating on the substrate and the resulting scattered diffraction orders.

FIG. 9 illustrates two light beams incident on the target grating 30 on the substrate W and the resulting scattered diffraction orders. The solid arrow 902 represents a light ray coming from point 716 in the illumination plane 714. The solid arrows −1, 0 and +1 represent the scattered negative first order, zeroth order and positive first order diffracted beams respectively originating from the incident beam 902. The dashed arrow 902' represents a light ray coming from point 716' in the illumination plane 714. The dashed arrows −1', 0' and +1' represent the scattered negative first order, zeroth order and positive first order diffracted beams respectively originating from the incident beam 902'. Each of the scattered beams has a band of wavelengths of light because a white light source is used. The asymmetry of the grating will affect the spectrum of light differently for the beams +1' and −1, for example if light is reflected differently from different left and right sidewalls. If there was no asymmetry in the grating, then those beams +1' and −1 would have the same spectral profile. Analysis of the differences in the spectral components of the +1' and −1 beams is used in embodiments of the present invention to determine the asymmetry of the target grating. In the case of stacked gratings in an overlay target, then the effect on the diffraction orders of an overlay error between the stacked grating may be similar to the effect of an asymmetric single grating. Analysis of the differences in the spectral components of the +1' and −1 beams may then be used in embodiments of the present invention to determine the overlay error in stacked grating overlay targets.

Embodiments of the present invention selectively detect properties (such as intensity as a function of wavelength) of two or more of the beams 0', +1', −1 and 0 to determine asymmetric properties of the target. For example, overlay error in a stacked overlay target can be determined by comparing the +1' and −1 beams, asymmetry in a single grating can be determined by comparing the +1' and −1 beams and asymmetry in a single or stacked target structure can be determined by detecting the 0', +1', −1 and 0 beams and using reconstruction.

With reference again to FIG. 7, the light that is scattered by the target grating 30 and the surrounding product area (802 in FIG. 8) is collimated by lens L3 and the double telecentric system L3 and L4 make a magnified image of the grating and product environment on the field stop FS. The field stop FS is placed at the image plane of the objective lens L3. The purpose of the field stop FS is to limit the spatial extent of the intermediate image and to suppress stray light in the detection optics. The spatial filter thus spatially filters radiation scattered from a surface of the substrate adjacent to the target to select radiation scattered by the target.

Lenses L4 and L5 re-image the pupil plane PP of the scattered light onto an achromatic quadrature wedge QW. This image 718 of the pupil plane has four components of the scattered light, 0, −1, 0' and +1'. The quadrature wedge QW redirects the light in the four quadrants of the pupil plane 718 in four different directions. Thus the quadrature wedge QW is an optical device configured to separately redirect diffraction orders of radiation scattered from the substrate. The quadrature wedge QW may comprise four wedges. As a result of the quadrature wedge QW, lens L6 produces, in the image plane IP, four spatially separated sub images 720 of the light that is transmitted by the aperture stop FS. Each of the four sub images 720 are the width WFS of the field stop FS. The central square in each sub-image represents the target grating and is surrounded by the product circuitry. Although the target grating is shown as a square, it may have another shape, such as a rectangle. The images 720 comprise two diagonally opposed images that contain the zeroth order images 0 and 0' and the two remaining diagonally opposed images contain the negative first and positive first order images −1 and +1'. The skilled person will appreciate that the arrangement of each of the four sub images in the image plane will depend on the wedge arrangement. Other arrangement of the sub images can therefore be achieved using different relative orientation of the wedges and/or one or more lenses L6. Furthermore, the sub images need not be arranged on the same plane.

As white light is used, the quadrature wedge is achromatic otherwise the image shift would become color-dependant. Achromatic wedges can be made in transmission but reflective wedges are also suitable since they are intrinsically achromatic.

Four multimode detection fibers MF are now used to capture the two zeroth order intensity components and the positive first and negative first order intensity components of the grating. Thus the fibers are a capturing device configured to capture one or more of the separately redirected diffraction orders. This is "selected area" detection that suppresses light from the product environment. The position of the fibers relative to the lenses is configured to capture the selected area of each sub image 720 corresponding to the target grating. Optionally, piezo micro manipulators may be used for a dynamic adjustment in the sensor.

Multimode fibers typically have core diameters of 200 μm and this diameter is smaller than the image of the grating in order to select light scattered by the grating in preference to that scattered by the surrounding product area. If the grating has a length of 10 μm then the magnification of the lens system L3, L4, L5 and L6 in this embodiment is at least 40.

The wedge angle is sufficiently large to allow a complete separation of the four sub images 720. If the separation is too small the images will overlap causing crosstalk from the product area into the grating area.

The broadband light that is captured by the detection fibers is sent to four spectrometers that are preferably nominally identical. These four spectrometers simultaneously and in parallel measure the intensities of the two zeroth orders $I_0(\lambda)$ and $I_0(\lambda)$ and positive first order $I_{+1}(\lambda)$ and negative first order $I_{-1}(\lambda)$ as a function of the wavelength. For overlay metrology a typical wavelength range could be 400-800 nm with a spectral resolution of 5 nm. This yields 80 pixels per spectrum so a grand total of about 320 samples. This measurement at the plurality of the wavelengths λ in the broadband light source can be acquired with very short acquisition times which enables high throughput.

In another, time multiplexed, embodiment, fewer than four spectrometers may be used and more than one separately captured diffraction orders are directed to a spectrometer one at a time for each measurement as a function of wavelength.

The four signals are measured for one given angle of incidence. The skilled person will appreciate that this can be repeated for more angles of incidence by changing the location of the illumination spot 708 in the illumination pupil plane 706.

The set of measured spectra can now be used in processor PU to calculate asymmetry properties of the target grating.

Asymmetry properties such as calculated overlay error (for a an overlay target with a stack of more than one superimposed grating) and asymmetry (for a single grating) can be determined by comparing the measured +1' and −1 spectra as in the Diffraction Based Overlay method.

Figure 10:
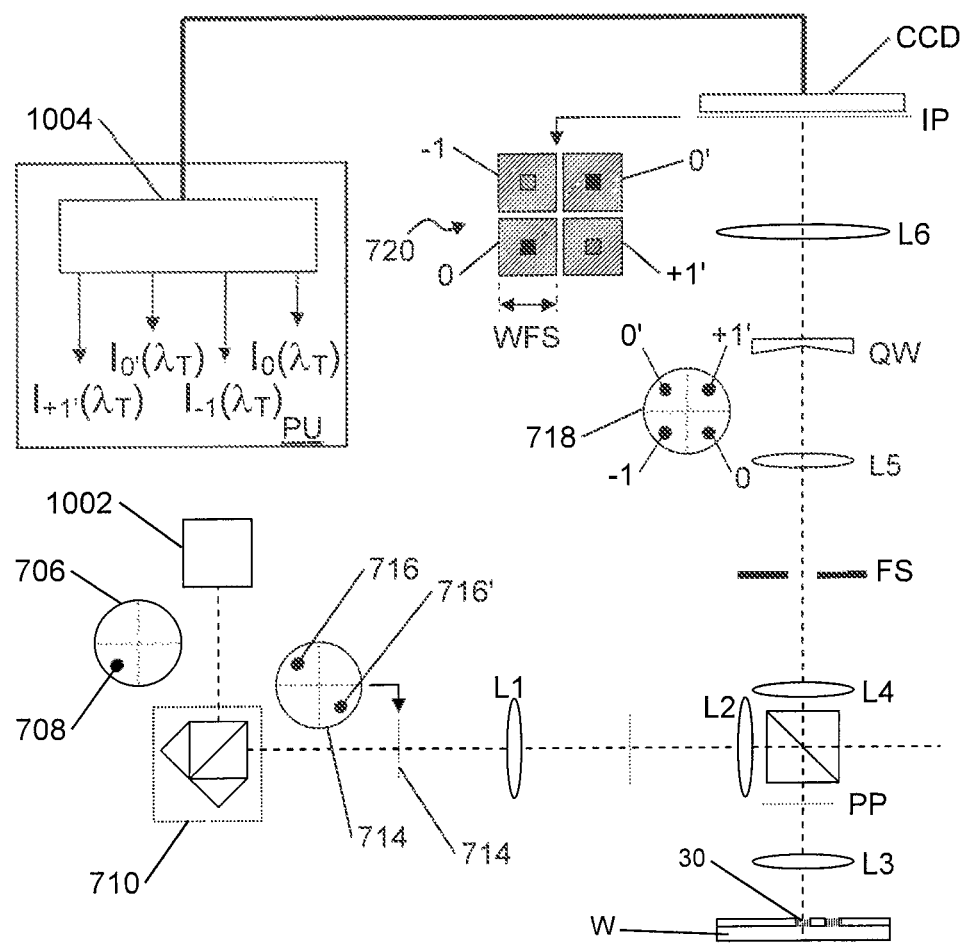
FIG. 10 illustrates an inspection apparatus according to an embodiment of the present invention with a tunable light source and CCD detector.

FIG. 10 shows an alternative embodiment. Elements in common with FIG. 7 have the same reference signs. Instead of using a white-light source, a single wavelength source 1002 is used. The single wavelength source may be tunable or switchable to provide a plurality of wavelengths. The single wavelength is denoted $\lambda_T$. For each single wavelength the image "720" is now projected on a detector such as a CCD camera which measures the intensities of the images formed by the minus first, positive first and zeroth orders. In this embodiment a pattern recognition software module 1004 executing on the processing unit PU is used to identify the area where the grating images are located and to extract the intensities of the two zeroth orders $I_0(\lambda_T)$ and $I_0(\lambda_T)$ and positive first order $I_{+1}(\lambda_T)$ and negative first order $I_{-1}(\lambda_T)$ at the wavelength $\lambda_T$. The wavelength $\lambda_T$ is thus adjusted and the measurements are repeated in series to determine the intensities of the two zeroth orders $I_0(\lambda)$ and $I_0(\lambda)$ and positive first order $I_{+1}(\lambda)$ and negative first order $I_{-1}(\lambda)$ at a plurality of the single wavelengths $\lambda_T$.

Asymmetry properties such as asymmetric structural parameters (for a single grating) and/or shape of the grating (for a single grating or a stacked grating overlay target) can be determined using reconstruction. This is achieved using a method similar to as described with reference to FIGS. 5 and 6. However, instead of modelling and measuring diffraction patterns, the intensity (and/or polarization) as a function of wavelength for the zeroth and first orders is measured and modeled. To model asymmetry, the 'model recipe' that defines the parameterized model of the target structure in terms of the parameters $p_i$ ($p_1$, $p_2$, $p_3$ and so on) includes parameters related to the target grating asymmetry. Such parameters are different left and right sidewall angles and rooftop shape. The model calculates the measured intensity (and/or polarization) parameters as a function of illumination wavelength.

Figure 11:
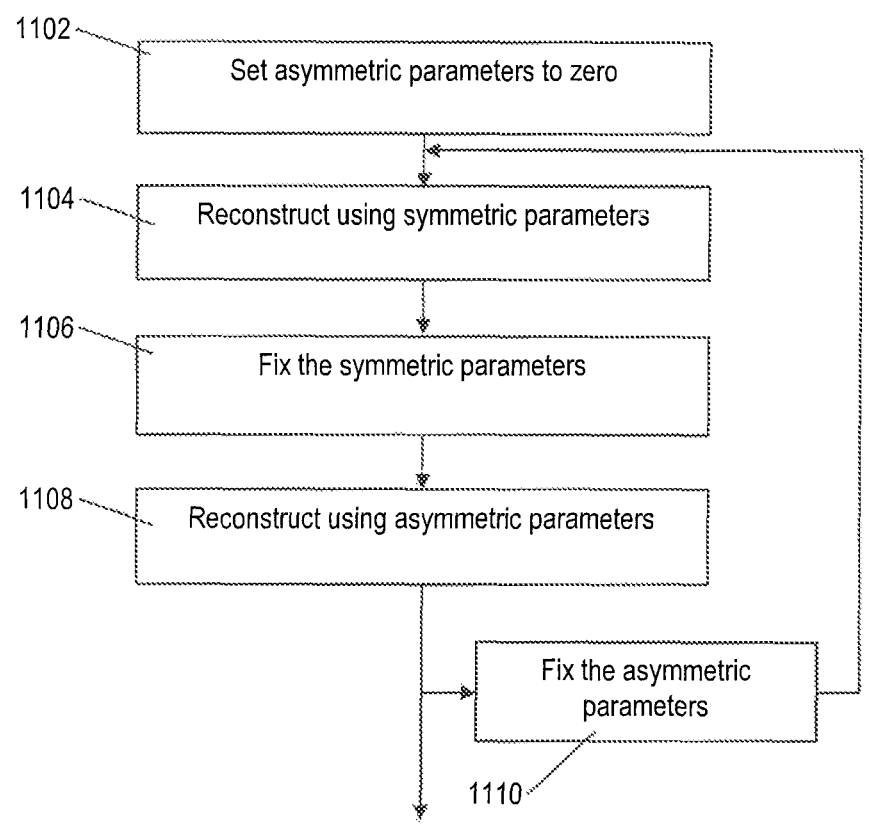
FIG. 11 is a flow chart of reconstruction using symmetric and asymmetric model parameters.

An approach to the modelling when symmetric and asymmetric parameters are used is shown in FIG. 11.

In step 1102: Set asymmetric parameters to zero.

In step 1104: Reconstruct using symmetric parameters until convergence is reached.

In step 1106: Fix the symmetric parameters so they are not modified.

In step 1108: Reconstruct using asymmetric parameters until convergence is reached.

In step 1110: Fix the asymmetric parameters so they are not modified.

Perform another iteration of steps 1104 to 1108 for small updates of the symmetric parameters.

In another embodiment, a reference branch can be added to compensate for intensity fluctuations in a manner that is similar to that described with reference to FIG. 4. Such an approach could involve adding another spectrometer.

The embodiments described above with reference to FIGS. 7 and 10 have point-mirrored illumination beams. This provides high measurement speed. Other embodiments could, however, also be realized with only one input beam that is sequentially switched to the point-mirrored position.

Although the measurement and modelling of intensity of diffracted light as a function of frequency is described with reference to FIGS. 7 and 10, embodiments of the present invention also include the measurement and modelling of the polarization state as a function of frequency using suitable ellipsometric or polarimetric techniques.

Advantages of embodiments of the present invention include: They enable process-robust overlay metrology on in-die gratings. Using multiple spectrometers for parallel data acquisition allows high throughput. The measurement of the zeroth order scattered light allows CD metrology as well as asymmetry.

Another embodiment is described with reference to FIGS. 12 to 15 below.

Instead of the achromatic quadrature wedge QW described with reference to FIG. 10, multiple single wedges MSW for particular respective angular spectra may be used.

Figure 12:
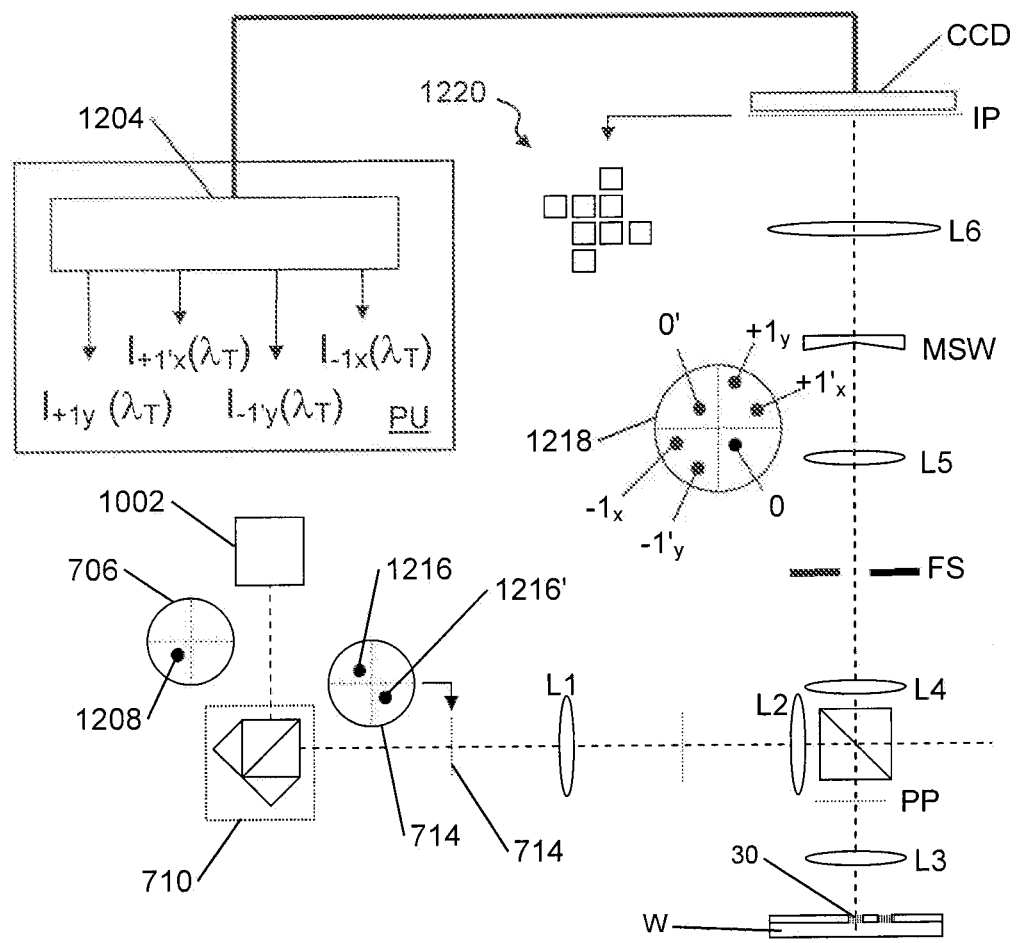
FIG. 12 illustrates an inspection apparatus according to an embodiment of the present invention with a tunable light source and CCD detector for separation of orders arising from x and y target periodicity.

FIG. 12 illustrates an inspection apparatus according to an embodiment of the present invention with a tunable light source and CCD detector for separation of orders arising from x and y target periodicity. In FIG. 12, elements in common with FIGS. 7 and 10 have the same reference signs. As for the embodiment of FIG. 10, a single wavelength source 1002 is used. The single wavelength source may be tunable or switchable to provide a plurality of wavelengths. The single wavelength is again denoted $\lambda_T$.

The illumination pupil 706 at the exit of the illuminator has one spot 1208. The single spot is positioned in the illumination pupil such that the combination of wavelength and target grating pitches (in x and y directions of target periodicity) results in the first diffraction orders scattered from the wafer in x and y being positioned apart in the image of the pupil plane 1218. This is described with reference to FIG. 13 below. Such positioning allows the first diffraction orders scattered from the wafer in x and y to be separated by the multiple single wedges MSW, as described below.

The pencil beam is sent through an "image copy-and-rotate" device 710. As a result of this copy action, the illumination pupil plane 714 is now illuminated with two identical single wavelength sources 1216, 1216' that are point-mirrored relative to the origin (and have substantially zero spatial frequency). As before, this provides a well-defined angle of incidence of illumination across the target that facilitates grating reconstruction. For this reason, the extent of the point sources is kept small.

Figure 15A:
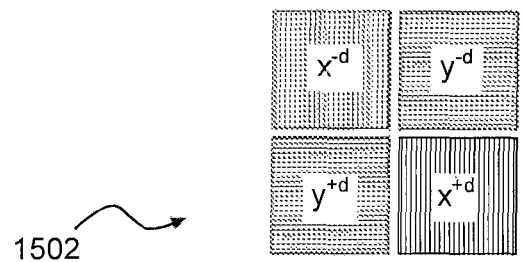
FIGS. 15A and 15B illustrate a compound target structure and efficient overlapping of target images at the sensor.

Lenses L1 and L2 form a double-telecentric system that image the illumination pupil into the pupil plane of the high-NA (numerical aperture) lens L3. This objective lens L3 illuminates the target 30 which may be a compound grating with areas periodic in a plurality of directions, for example having separate x and y gratings as illustrated by FIG. 15a. Alternatively, the x and y periodicity may be in the same 2-dimensional grating, for example with an array of rectangles or circles. The target may be surrounded by an unknown product pattern. Lenses L1, L2 and L3 thus form an optical system that illuminates the target via the objective. The illumination spot on the wafer is normally chosen much larger than the target grating(s). Typical values are, for example, a spot diameter of 30 μm projected on the wafer and grating size of 10×10 μm². The embodiment will still work when the illumination spot is smaller than the grating, for example with a relatively large grating in a scribe lane.

The light that is scattered by the target grating 30 and the surrounding product area is collimated by lens L3 and the double telecentric system L3 and L4 make a magnified image of the grating and product environment on the field stop FS. The field stop FS is placed at the image plane of the objective lens L3. The purpose of the field stop FS is to limit the spatial extent of the intermediate image and to suppress stray light in the detection optics. The spatial filter thus spatially filters radiation scattered from a surface of the substrate adjacent to the target to select radiation scattered by the target.

Lenses L4 and L5 re-image the pupil plane PP of the scattered light onto a multiple single wedge optical device MSW. This image 1218 of the pupil plane has six components of the scattered light, 0', +1$_y$, +1'$_x$, 0, -1'$_y$ and -1$_x$. The multiple single wedge MSW device blocks or discards the $0^{th}$ order diffracted light 0' and 0 and redirects the light of the +1$_y$, +1'$_x$, -1'$_y$ and -1$_x$ orders in four different respective directions. Thus the multiple single wedge MSW is an optical device configured to separately redirect diffraction orders of radiation scattered from the substrate. Furthermore, it is configured to separate diffraction orders of radiation that are scattered from the substrate in a plurality of periodicity directions, in this example x and y.

The $0^{th}$ order radiation may be tapped and directed into another branch of the optical system, or to another unused part of the image sensor CCD, for intensity measurement to correct for intensity variation. Thus the $0^{th}$ order intensity may for example be measured at the same time as the spectrum measurements or at the start of each batch of wafer substrates being measured.

Figure 14A:
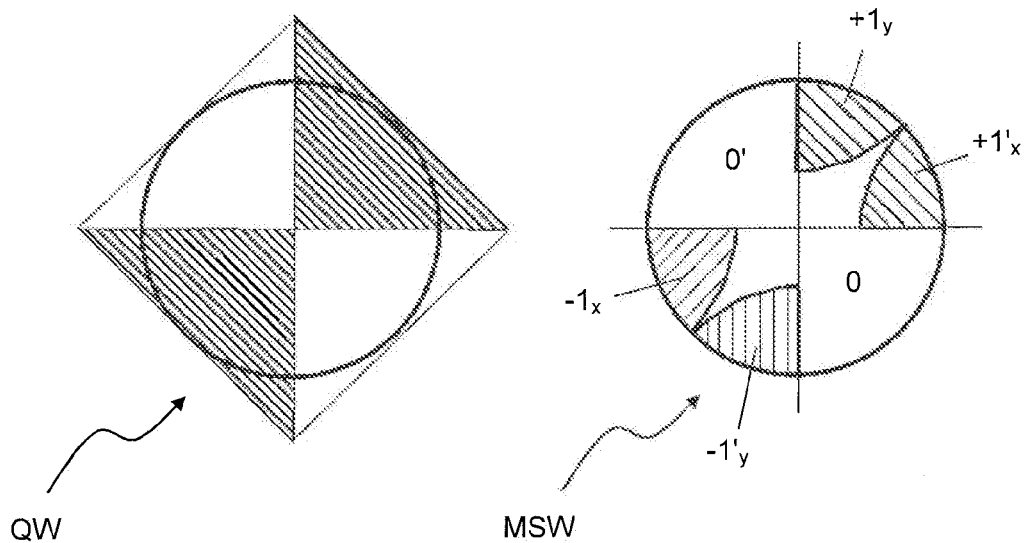
FIGS. 14A and 14B illustrate wedge configurations and the resulting images of the target at the sensor.

FIG. 14 illustrates wedge configurations QW and MSW and the resulting images 1420 and 1220 of the target at the sensor. The multiple single wedge MSW may comprise four wedges as illustrated in FIG. 14a. The shape in plan view is not limited to that shown in FIG. 14a, which results from grinding flats on a spherical lens.

Figure 14B:
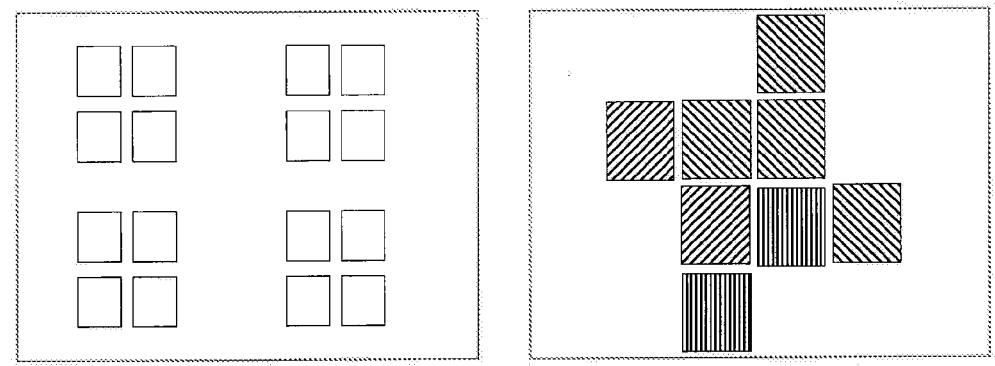

Returning to FIG. 12, as a result of the configuration of the multiple single wedge MSW, lens L6 produces, in the image plane IP, four sub images 1220 of the light that is transmitted by the aperture stop FS, spatially separating the orders arising from target periodicity in x and y. These are illustrated in FIG. 14b and enlarged in FIG. 15b with hatching drawn to match the corresponding wedge of the multiple single wedge MSW. For example the +1'$_x$ wedge in FIG. 14a gives rise to the sub image with corresponding hatching in FIG. 14a and labeled +1'$_x^{-d}$ and +1'$_x^{+d}$ in FIG. 15b. Each sub image comprising a pair of squares with the same hatching represents the target grating. The surrounding product circuitry has been spatially filtered by the field stop FS. Although the target gratings are shown as a square, they may have another shape, such as a rectangle. The images 1220 comprise spatially overlapped images of the target arising from the +1$_y$, +1'$_x$, -1'$_y$ and -1$_x$ orders. Thus the multiple single wedge optical device MSW is configured to project the separated diffraction orders onto the one or more detectors to form spatially overlapped images of the target arising from different separated diffraction orders.

The skilled person will appreciate that the arrangement of each of the four sub images in the image plane will depend on the wedge arrangement. Other arrangement of the sub images can therefore be achieved using different relative orientation of the wedges and/or one or more lenses L6. Furthermore, the sub images need not be arranged on the same plane.

Figure 15B:
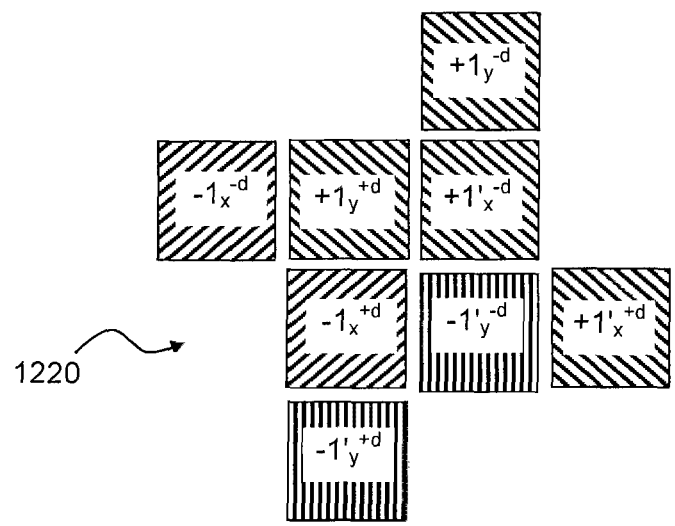

The advantage of the arrangement of sub images 1220 shown in FIGS. 12, 14b and 15b is that more of the detection sensor CCD area can be utilized (more pixels), enabling improved TMU and reduced measurement time, compared to the spatially separated sub images (1420 in FIG. 14b) produced by the quad wedge QW (illustrated in FIG. 14a) in accordance with the embodiment described with reference to FIG. 10. In this example the overlapping of sub images provides an efficient arrangement of images of the biased composite grating. It will be appreciated that other overlapping or mosaiced arrangements of sub images to suit specific target layouts while efficiently covering the image sensor are envisaged.

The multiple single wedge MSW may be achromatic to avoid wavelength dependent image shift. Achromatic wedges can be made in transmission but reflective wedges are also suitable since they are intrinsically achromatic.

For each single wavelength $\lambda_T$ the image 1220 is now projected on a detector such as a CCD camera which measures the intensities of the images formed by the minus first and positive first orders. In this embodiment a pattern recognition software module 1004 executing on the processing unit PU is used to identify the area where the grating images are located and to extract the intensities $I_{+1y}(\lambda_T)$, $I_{+1'x}(\lambda_T)$, $I_{-1'y}(\lambda_T)$ and $I_{-1x}(\lambda_T)$ of the +1$_y$, +1'$_x$, -1'$_y$ and -1$_x$ orders at the wavelength $\lambda_T$. The wavelength $\lambda_T$ is thus adjusted and the measurements are repeated in series to determine the intensities $I_{+1y}(\lambda)$, $I_{+1'x}(\lambda)$, $I_{-1'y}(\lambda)$ and $I_{-1x}(\lambda)$ at a plurality of the single wavelengths $\lambda_T$.

Figure 13A:
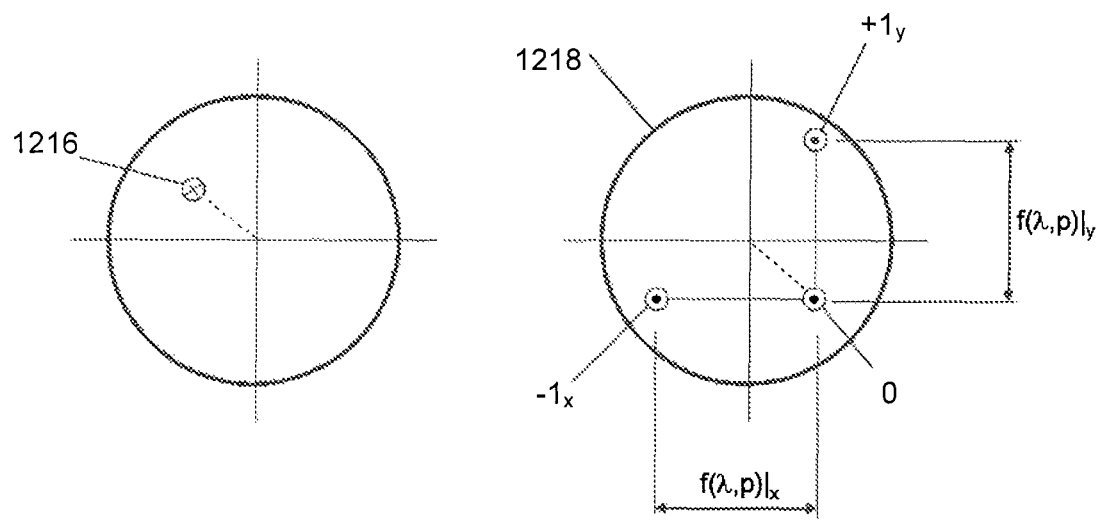
FIGS. 13A and 13B illustrate the separation in the pupil plane image of the orders arising from x and y target periodicity.

FIG. 13 illustrates the separation in the pupil plane of the orders arising from x and y target periodicity. With reference to FIG. 13a, only one illumination spot 1216 is considered. It gives rise in the pupil plane image 1218 to $0^{th}$ order spot 0. Diffraction resulting from periodicity in the y direction gives rise to the positive first order spot $+1_y$ offset in the y direction the $0^{th}$ order spot in pupil plane image 1218 by a distance that is a function of the illumination wavelength $\lambda$, and the grating pitch in the y direction, p. The negative first order spot $-1_y$ falls outside the pupil image and is not present.

Diffraction resulting from periodicity in the x direction gives rise to negative first order spot $-1_x$ offset in the x direction from the $0^{th}$ order spot by a distance that is a function of the illumination wavelength $\lambda$, and the grating pitch in the x direction. In this example the grating pitch in the x direction is p, the same as in the y direction, although it could be different from the pitch in the y direction. The positive first order spot $+1_x$ falls outside the pupil image and is not present.

Figure 13B:
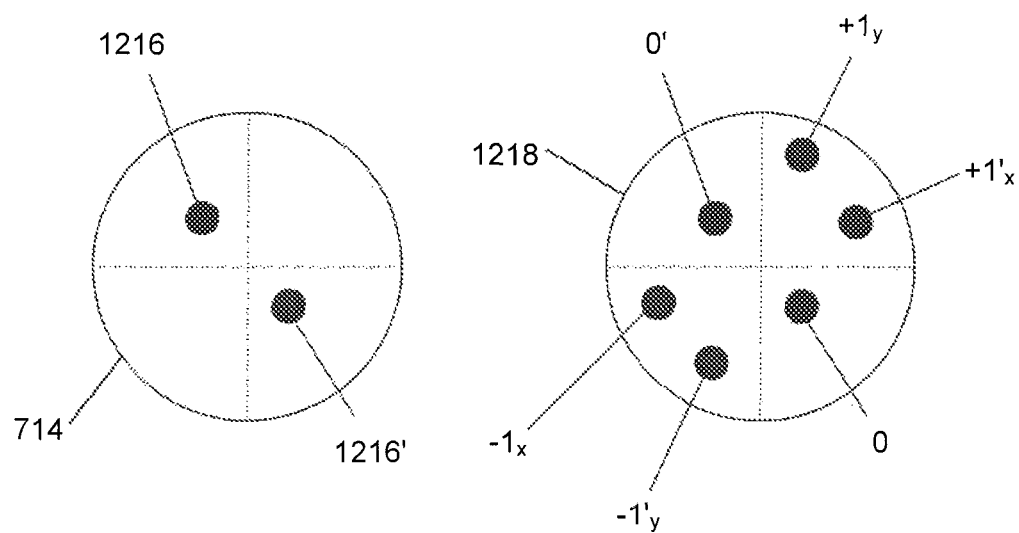

FIG. 13b shows the illumination pupil plane 714 illuminated with two point sources 1216 and 1216', by the action of the image copy-and-rotate device 170, as shown in FIG. 12. In the same way as described for FIG. 13a, the illumination spot 1216' gives rise to diffraction orders $+1'_x$ and $-1'_y$ in the pupil plane image 1218.

FIG. 15 illustrates a compound target structure 1502 and an enlarged view of the efficient overlapping of target sub images 1220 at the sensor, as shown in FIGS. 12 and 14b. In the target structure 1502, the periodicity of each target is denoted by x and y and illustrated (not to scale) with the vertical and horizontal hatching respectively. The superscript −d and +d denotes an overlay bias applied to each grating, as is known for calculation of overlay offsets using a biased composite grating as described in patent publication U.S. Pub. App. No. 2010/0328655, which is incorporated by reference herein in its entirety.

Asymmetry properties such as asymmetric structural parameters (for a single grating) and/or shape of the grating (for a single grating or a stacked grating overlay target) can be determined using reconstruction. This is achieved using a method similar to as described with reference to FIGS. 5 and 6. However, instead of modelling and measuring diffraction patterns, the intensity (and/or polarization) as a function of wavelength for the first orders is measured and modeled. To model asymmetry, the 'model recipe' that defines the parameterized model of the target structure in terms of the parameters $p_i$ ($p_1$, $p_2$, $p_3$ and so on) includes parameters related to the target grating asymmetry. Such parameters are different left and right sidewall angles and rooftop shape. The model calculates the measured intensity (and/or polarization) parameters as a function of illumination wavelength.

As for the embodiments described with reference to FIGS. 7 and 10, an approach to the modelling when symmetric and asymmetric parameters are used is shown in FIG. 11.

The inspection apparatus and method of inspection embodiments described herein may be used in methods of device manufacturing and may be incorporated into lithographic apparatuses and lithographic processing cells.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the present invention in the context of optical lithography, it will be appreciated that the present invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the present invention have been described above, it will be appreciated that the present invention may be practiced otherwise than as described. For example, the present invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the present invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the present invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An inspection apparatus for determining, asymmetry properties of a target on a substrate, the target being periodic in a plane of the substrate, the inspection apparatus comprising:
   an illumination system configured to provide a plurality of wavelengths of radiation;
   an optical system comprising an objective and configured to illuminate the target via the objective with the radiation from a first direction and a second direction reflected with respect to the plane of the substrate;
   an optical device configured to separately redirect diffraction orders of radiation scattered from the substrate;
   one or more detectors configured to measure properties of the separately redirected diffraction orders at the plurality of wavelengths; and
   a processor configured determine the asymmetry properties of the target using the properties measured at the plurality of wavelengths.

2. The inspection apparatus of claim 1, wherein the illumination system is configured to provide two beams of radiation point mirrored with respect to a pupil plane of the objective.

3. The inspection apparatus of claim 1, wherein the optical device is configured to separate diffraction orders of radiation scattered from the substrate by illumination from each of the first and second directions.

4. The inspection apparatus of claim 3, wherein the target is periodic in a plurality of periodicity directions and the optical device is configured to separate diffraction orders of radiation that are scattered from the substrate in the plurality of periodicity directions.

5. The inspection apparatus of claim 4, wherein the optical device is configured to project the separated diffraction orders onto the one or more detectors to form spatially overlapped images of the target arising from different separated diffraction orders.

6. The inspection apparatus of claim 1, wherein the illumination system comprises a broadband light source.

7. The inspection apparatus of claim 1, further comprising a spatial filter at an image plane of the objective configured to spatially filter radiation scattered from a surface of the substrate adjacent to the target to select radiation scattered by the target.

8. The inspection apparatus of claim 1, wherein the optical device is located at a pupil plane of the objective.

9. The inspection apparatus of claim 1, wherein the optical device comprises four wedges configured to separately redirect radiation from each of four quadrants.

10. The inspection apparatus of claim 1, wherein the target is periodic in a plurality of periodicity directions and the optical device comprises a plurality of surfaces each corresponding to respective diffraction orders of radiation that are scattered from the substrate in the plurality of periodicity directions.

11. The inspection apparatus of claim 1, wherein the optical device is achromatic.

12. The inspection apparatus of claim 1, further comprising a capturing device configured to capture one or more of the separately redirected diffraction orders.

13. The inspection apparatus of claim 12, wherein the capturing device comprises one or more optical fibers.

14. The inspection apparatus of claim 12, wherein the capturing device is configured to spatially filter the radiation scattered from the substrate to select, radiation scattered by the target.

15. The inspection apparatus of claim 1, wherein the measured properties comprise intensity at the plurality of wavelengths.

16. The inspection apparatus of claim 1, wherein the detector comprises a spectrometer.

17. The inspection apparatus of claim 1, wherein the measured properties comprise polarization as a function of wavelength.

18. A method of determining asymmetry properties of a target on a substrate, the target being periodic in a plane of the substrate, the method comprising:
   illuminating the target via an objective with radiation from a first direction and a second direction reflected with respect to the plane of the substrate;
   separately redirecting diffraction orders of radiation scattered from the substrate;
   measure properties of the separately redirected diffraction orders at a plurality of wavelengths using one or more detectors; and
   determining asymmetry properties of the target using the properties measured at the plurality of wavelengths.

19. A lithographic apparatus comprising:
   an illumination system configured to illuminate a pattern;
   a projection system configured to project an image of the pattern on to a substrate; and
   an inspection apparatus configured to determine asymmetry properties of a target on a substrate, the target being periodic in a plane of the substrate, the inspection apparatus comprising:
   an illumination system configured to provide a plurality of wavelengths of radiation;
   an optical system comprising an objective and configured to illuminate the target via the objective with the radiation from a first direction and a second direction reflected with respect to the plane of the substrate;
   an optical device configured to separately redirect diffraction orders of radiation scattered from the substrate;
   one or more detectors configured to measure properties of the separately redirected diffraction orders at the plurality of wavelengths; and
   a processor configured determine asymmetry properties of the target using the properties measured at the plurality of wavelengths.

20. A lithographic cell comprising:
   a coater arranged configured to coat substrates with a radiation sensitive layer;
   a lithographic apparatus configured to expose images onto the radiation sensitive layer of substrates coated by the coater;
   a developer configured to develop images exposed by the lithographic apparatus; and
   an inspection apparatus for determining asymmetry properties of a target on a substrate, the target being periodic in a plane of the substrate, the inspection apparatus comprising:

an illumination system configured to provide a plurality of wavelengths of radiation;

an optical system comprising an objective and configured to illuminate the target via the objective with the radiation from a first direction and a second direction reflected with respect to the plane of the substrate;

an optical device configured to separately redirect diffraction orders of radiation scattered from the substrate;

one or more detectors configured to measure properties of the separately redirected diffraction orders at the plurality of wavelengths; and a processor configured determine asymmetry properties of the target using the properties measured at the plurality of wavelengths.

21. A device manufacturing method comprising:

using a lithographic apparatus to form a pattern on a substrate; and determining a value related to a parameter of the pattern by:

providing a plurality of wavelengths of radiation;

illuminating a target, formed using the lithographic apparatus, via an objective with the radiation from a first direction and a second direction reflected with respect to the plane of the substrate;

separately redirecting diffraction orders of radiation scattered from the substrate;

measuring properties of the separately redirected diffraction orders at the plurality of wavelengths using one or more detectors; and determining asymmetry properties of the target using the properties measured at the plurality of wavelengths.

* * * * *

UNITED STATES PATENT AND TRADEMARK OFFICE
CERTIFICATE OF CORRECTION

PATENT NO. : 9,223,227 B2
APPLICATION NO. : 13/361349
DATED : December 29, 2015
INVENTOR(S) : Bhattacharyya et al.

Page 1 of 1

It is certified that error appears in the above-identified patent and that said Letters Patent is hereby corrected as shown below:

In the claims

In column 21, line 15, claim 1, please delete ",".

Signed and Sealed this
Twelfth Day of April, 2016

Michelle K. Lee
*Director of the United States Patent and Trademark Office*